United States Patent
Doo

(10) Patent No.: US 8,499,618 B2
(45) Date of Patent: Aug. 6, 2013

(54) DEVICE FOR AUTOMATICALLY MEASURING VISCOSITY OF LIQUID

(75) Inventor: Jae Kyun Doo, Jeonju (KR)

(73) Assignee: Bio-Visco Inc., Jeonju (KR)

( * ) Notice: Subject to any disclaimer, the term of this patent is extended or adjusted under 35 U.S.C. 154(b) by 272 days.

(21) Appl. No.: 12/891,603

(22) Filed: Sep. 27, 2010

(65) Prior Publication Data

US 2011/0072890 A1   Mar. 31, 2011

(30) Foreign Application Priority Data

Sep. 25, 2009  (KR) .................... 20-2009-0012636 U
Nov. 16, 2009  (KR) ........................ 10-2009-0110545

(51) Int. Cl.
*G01N 11/04*   (2006.01)
*G01N 11/00*   (2006.01)

(52) U.S. Cl.
USPC ........................................ 73/54.05; 73/54.01

(58) Field of Classification Search
USPC ............ 73/54.01, 54.05, 54.11, 54.14, 54.43; 422/63, 64, 67, 501, 509, 546
See application file for complete search history.

(56) References Cited

U.S. PATENT DOCUMENTS

| | | | | |
|---|---|---|---|---|
| 3,720,097 A * | 3/1973 | Kron | ........................... | 73/54.04 |
| 4,858,127 A * | 8/1989 | Kron et al. | .................... | 73/54.09 |
| 5,257,529 A * | 11/1993 | Taniguchi et al. | ............ | 73/54.09 |
| 6,322,524 B1 * | 11/2001 | Kensey et al. | ................. | 600/573 |
| 6,624,435 B2 * | 9/2003 | Kensey et al. | ................. | 250/577 |
| 6,692,437 B2 * | 2/2004 | Kensey et al. | ................. | 600/300 |
| 6,732,573 B2 * | 5/2004 | Shin et al. | ..................... | 73/54.04 |
| 6,745,615 B2 * | 6/2004 | Kensey et al. | ............... | 73/54.04 |
| 6,796,168 B1 * | 9/2004 | Goldstein et al. | ............ | 73/54.01 |
| 6,807,849 B1 * | 10/2004 | Reed et al. | .................... | 73/60.11 |
| 6,907,772 B2 * | 6/2005 | Kensey et al. | ............... | 73/54.04 |
| 2003/0226391 A1 * | 12/2003 | Sanderson et al. | ............. | 73/1.36 |

FOREIGN PATENT DOCUMENTS

WO         0136936        5/2001

* cited by examiner

*Primary Examiner* — Hezron E Williams
*Assistant Examiner* — David Z Huang
(74) *Attorney, Agent, or Firm* — Kunzler Law Group, PC

(57) ABSTRACT

A device for automatically taking out a sample liquid contained in a reservoir and measuring the viscosity of the liquid is described herein. In one embodiment, the device includes a base body and a transferring part provided on the stage of the base body for taking the sample liquid out of the reservoir and supplying the sample liquid to a viscosity measuring part. The viscosity measuring part is provided on the stage for measuring the viscosity of the sample liquid supplied from the transferring part. The device also includes a control part for controlling operations of the transferring part and the viscosity measuring part. Additionally, the device includes a display part for displaying the results measured by the viscosity measuring part.

15 Claims, 13 Drawing Sheets

DEVICE FOR AUTOMATICALLY MEASURING VISCOSITY OF LIQUID

CROSS-REFERENCE TO RELATED APPLICATIONS

This application claims the benefit of Korean Utility Application No. 20-2009-0012636, filed on Sep. 25, 2009 in the Korean Intellectual Property Office, and Korean Patent Application No. 10-2009-0110545, filed on Nov. 16, 2009 in the Korean Intellectual Property Office, the disclosure of both applications are incorporated herein by reference.

FIELD

This invention relates to a device for measuring viscosity, and more particularly, relates to an automatic viscometer which can perform a series of processes, such as keeping a reservoir containing a sample liquid, for example blood, at body temperature, extracting a fixed quantity of the liquid precisely, and measuring the viscosity of the liquid.

BACKGROUND

Conventional blood viscosity measurement devices deform blood between two controlled surfaces or, alternatively, let blood move from a human body to a flow restrictor tube and measure flow characteristics such as the flow resistance during the blood movement in the tube, in order to measure the viscosity of the blood or the aggregation ratio of blood cells.

PCT Published Patent Application No. WO01/036936 discloses a dual riser/single capillary viscometer. The viscometer monitors the change in height of two, oppositely-moving, columns of blood from the circulating blood of a patient and, given the dimensions of a capillary tube through which the blood flows, determines the blood viscosity over a range of shears, especially low shears. The system includes a tube set (disposable or non-disposable) that includes a pair of riser tubes, a capillary tube of predetermined dimensions that is coupled between the riser tubes (or that forms a portion of one riser tube) and a valve mechanism for controlling the circulating flow of blood from the patient into the riser tubes. Respective sensors monitor the movement of the columns of blood in each of the riser tubes and an associated microprocessor analyzes these movements, along with the predetermined dimensions of the capillary tube, to determine the viscosity of the patient's circulating blood.

To supply a blood sample to measure viscosity, a viscometer may obtain blood directly from a needle or tube connected to a vein or indirectly from a reservoir containing blood. Conventional reservoirs are evacuated tubes (or "Vacutainers"), such that they can supply blood by applying a predetermined pressure of air or other gas into the reservoirs. FIG. 1 is a front view illustrating one example of a conventional blood transferring device using air. The conventional blood transferring device of FIG. 1, which supplies blood manually, comprises a reservoir 20 including a silicone packing 25 on its top, a blood needle 30 passing through the silicone packing 25 and reaching the blood of the reservoir 20, an air needle 40 passing through the silicone packing 25, the end of which is located above the fluid level of the blood, and a syringe 50 for supplying air into the reservoir 20 via the air needle 40.

As an operator slowly introduces air into the reservoir using the syringe 50, the air injected via the air needle 40 produces a relatively higher pressure on the fluid level of the blood, and subsequently the higher pressure in the reservoir pushes the blood to the blood viscometer 60 through the blood needle 30. However, when the operator operates the syringe 50 manually, it is practically impossible to transfer the blood under a contant pressure and flow because it is very difficult to maintain a constant injection rate of air to the vaccum reservoir. Moreover, since the air needle 40 and the blood needle 30 are installed independently and controlled to different heights relative to the fluid level of the blood, it is difficult to precisely position both needles at the desired locations within the reservoir.

Additionally, because the two needles 30, 40 are physically separated, it is substantially difficult to automate the blood delivery system for the viscosity measurement of blood. For example, when introducing two needles 30, 40 through the silicone packing, the needles may be bent or curved. Moreover, when the needles 30 and 40 are removed from the rubber packing 25 at the end of a blood viscosity measurement, the needles may not be smoothly pulled out or may suddenly spring out. Accordingly, even with special precautions, an operator can be injured by a removed needle contaminated by a patient's blood, as well as be exposed to the risk of being infected by blood-borne diseases.

SUMMARY

The subject matter of the present application has been developed in response to the present state of the art, and in particular, in response to the problems and needs in the art that have not yet been fully solved by currently available liquid viscosity measurement devices. Accordingly, the subject matter of the present application has been developed to provide an automatic liquid viscosity measurement device that overcomes at least some of the above or other shortcomings of prior art liquid viscosity measurement devices and techniques.

For example, in certain implementations, the subject matter of the present disclosure provides an automatic viscometer that can automatically perform a series of processes, such as the maintenance of a sample liquid at a predetermined body temperature prior to the viscosity measurement, automatic needle injection, and automatic delivery of an exact quantity of liquid. In yet some implementations, the subject matter of the present disclosure provides an automatic viscometer with two needles that handle both air flow and blood flow, as well as needle introduction and removal processes that are automated for easy operation during an automatic blood viscosity measurement. Also, in some implementations, the subject matter of the present disclosure provides an automatic viscometer that can prevent an operator from being injured by the needles or exposed to the blood while introducing and removing the needles, and that can complete desired processes safely and quickly. Moreover, in certain implementations, the subject matter of the present disclosure includes an automatic viscometer that can reduce potential mistakes by and dependency on an operator, whose efficiency is dictated by the operator's experience, by providing an automated viscosity measurement device operable under uniform and consistent test conditions when repeated multiple times.

According to one exemplary embodiment, a device for automatically taking out a sample liquid contained in a reservoir and measuring the viscosity of the liquid comprises a base body. The device also comprises a transferring part provided on a stage of the base body for taking the sample liquid out of the reservoir and supplying the sample liquid to a viscosity measuring part provided on the stage for measuring the viscosity of the sample liquid supplied from the sample transferring part. Additionally, the device comprises a control part for controlling the operations of the transferring part and the viscosity measuring part. Further, the device comprises a display part for displaying the result measured by the viscosity measuring part.

According to certain implementations, the transferring part transports the sample liquid from the reservoir to the viscosity measuring part, such that the sample liquid can be introduced to the viscosity measuring part precisely at a predetermined velocity or flow. Because the control part controls in automated fashion and sequence the following: the extraction of the sample liquid from the reservoir, the transportation from the reservoir to the viscosity measuring part, and the actual viscosity measurement, the device of the present disclosure can obtain the viscosity measurement result with high reliability.

In some implementations, the transferring part does not expose the sample liquid, for example blood, to the atmosphere during the introduction of the liquid to the viscosity measuring part. Additionally, in some implementations, the transferring part maintains the blood at a desired body temperature (e.g., about 36.5° C.), such that the transferring part can transfer the liquid without raising the concern of altering properties of the liquid and can take accurate measurements of the liquid viscosity without unnecessary delay.

According to certain implementations, the transferring part comprises a reservoir receiving member for receiving the reservoir. Further, the transferring part comprises a liquid supplying member including a needle section positioned adjacent to the reservoir received in the reservoir receiving member. The liquid supplying member supplies the sample liquid from the reservoir to the viscosity measuring part. The transferring part also comprises a needle securing section to secure the needle at an upper part of the reservoir. Moreover, the transferring part includes a distance adjusting member for adjusting the distance between the reservoir and the needle section. Also, the transferring part comprises a pressurized gas supply member for supplying a pressurized gas into the reservoir through the needle section. Alternatively, the needle is in a fixed position and the reservoir can be moved toward the needle such that the desired distance between the needles and the liquid level can be obtained.

The distance adjusting member can adjust the distance between the needle section and the reservoir, so that the needle section may be inserted into or removed from the reservoir. After the needle section is at least partially inserted into the reservoir, the pressurized gas, for example air, is supplied into the reservoir via the needle section by the pressurized-gas supply member and the sample liquid may be transferred from the reservoir to the viscosity measuring part via the needle section. After transferring the sample liquid to the viscosity measuring part by the needle section, the pressurized gas supply member stops its operation (i.e., stops supplying pressurized gas into the reservoir) and subsequently the sample liquid stops moving through the needle section from the reservoir. In this manner, the sample liquid can be transferred automatically without the manual involvement of an operator. The pressurized-gas supply member can accurately supply pressurized gas to the reservoir with a predetermined constant pressure and flow using a stepping motor or a precision micro-pumping machine.

Although the needle section can use two separate needles to supply pressurized gas and transfer the liquid sample, the double needle system using a needle inside a needle configuration in the present disclosure has a superior resistance against bending and can be easily inserted into and removed from the reservoir. For example, the double needle system in the present disclosure may comprise an inner needle which is elongated and hollow, an outer needle relatively shorter than the inner needle, and a T-shaped fixing body fixing both the inner needle and the outer needle. Both the inner and outer needles are hollow, and form fluidic paths for the liquid sample and pressure gas, respectively. In the T-shaped fixing body, provided are a fluidic path connecting the inner needle and the viscosity measuring part and another fluidic path connecting the outer needle and the pressurized gas supply member for the pressurized gas. The two needles in the double needle system may be simultaneously inserted (e.g., driven by the distance adjusting member) into the reservoir through its rubber packing. In the double needle system, the pressurized gas such as air may be supplied via the fluidic path for the pressurized gas, whereas the inner needle, with one end portion of being submerged in the sample liquid in the reservoir, transfers the sample liquid from the reservoir to the viscosity measuring part.

In certain implementations, the automatic viscosity measurement device of the present disclosure can perform a plurality of processes automatically, such as the maintenance of a sample liquid at a predetermined constant temperature, the introduction of a double needle system into a reservoir that contains liquid sample, the transportation of a predetermined amount of the sample liquid, and the measurement of the viscosity of the liquid.

According to some implementations, because the introduction and removal of the two needles are executed without the manual involvement of an operator by the liquid-transferring part, and a sample liquid is transferred and treated automatically without the manual involvement of an operator, there is substantially no risk for the operator to be injured by needles contaminated by blood. Hence, the viscosity measurement process can be completed safely and quickly.

The automatic viscosity measurement device of this disclosure, through its automated processes, can help to reduce potential operator mistakes that might be introduced by manual operation steps, minimize the dependence on the operator's experience, and obtain reliable and accurate results under identical test conditions when multiple tests are conducted.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

Furthermore, the described features, advantages, and characteristics of the subject matter of the present disclosure may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments. These features and advantages will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Figure 1:
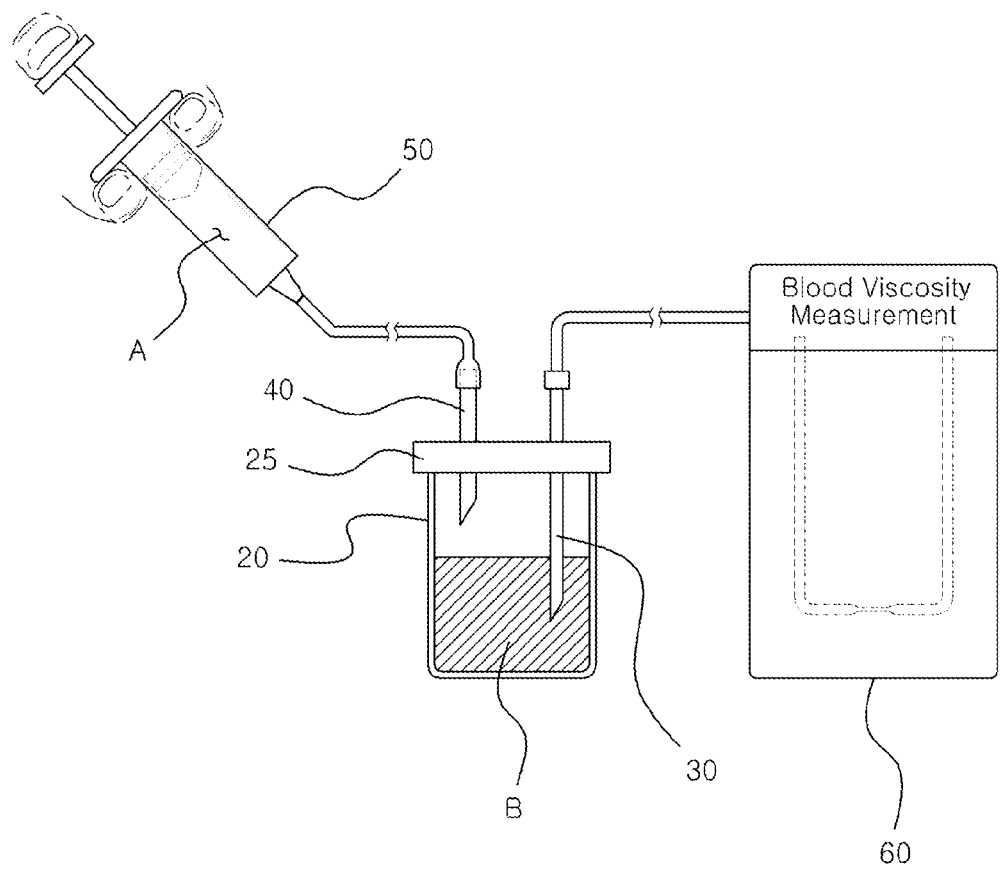
FIG. 1 is a side view illustrating a conventional blood transferring device using air.

Reference will now be made in detail to embodiments of the present disclosure, examples of which are illustrated in the accompanying drawings, wherein like reference numerals refer to the like elements throughout. The embodiments are described below in order to explain the present disclosure by referring to figures. Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Furthermore, the described features, structures, or characteristics of the subject matter described herein may be combined in any suitable manner in one or more embodiments. In the following description, numerous specific details are provided, such as examples of controls, structures, devices, algorithms, programming, software modules, user selections, hardware modules, hardware circuits, hardware chips, etc., to provide a thorough understanding of embodiments of the subject matter. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the disclosed subject matter.

Figure 2:
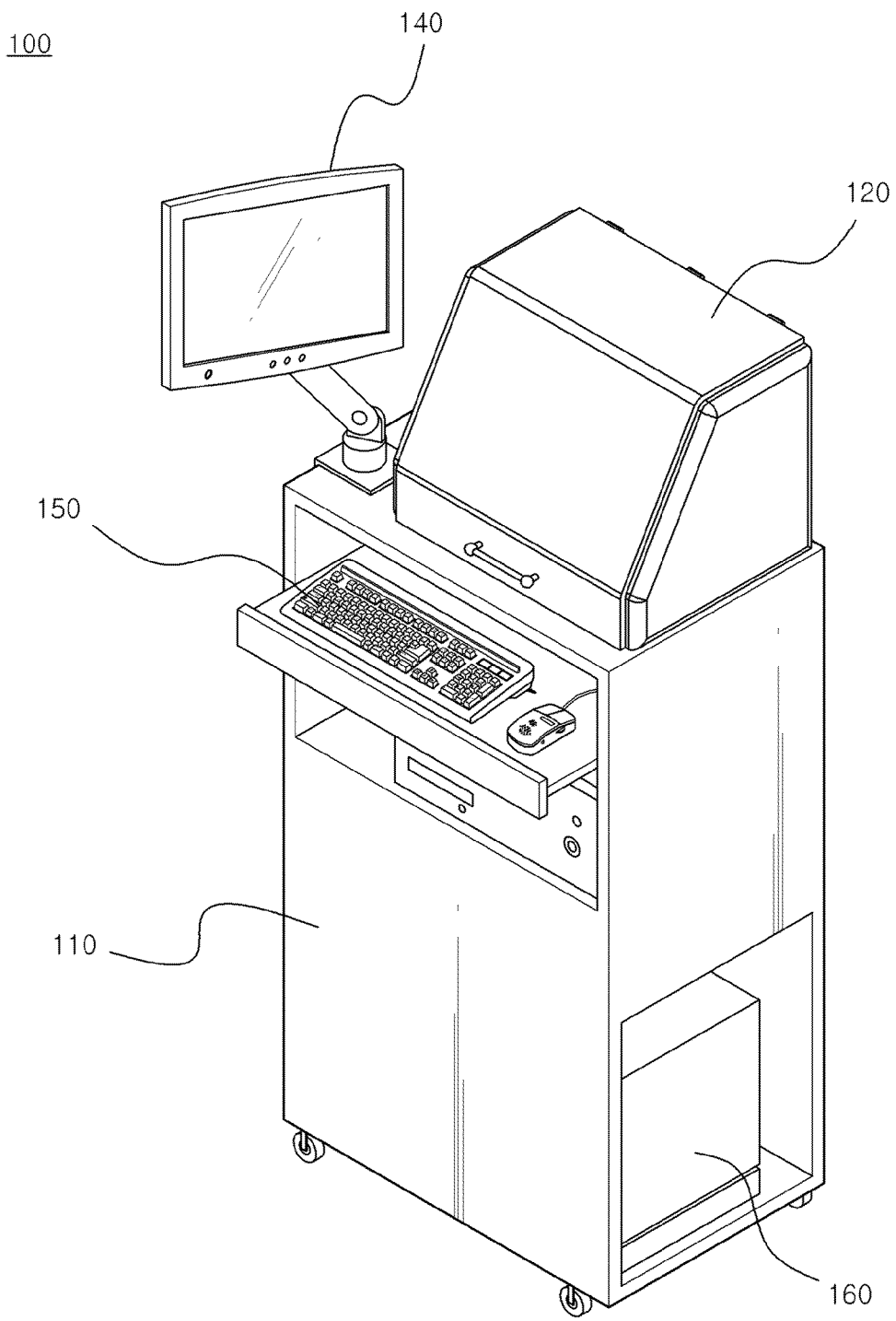
FIG. 2 is a frontal perspective view of a viscosity measurement device according to one embodiment of the present disclosure.
Figure 3:
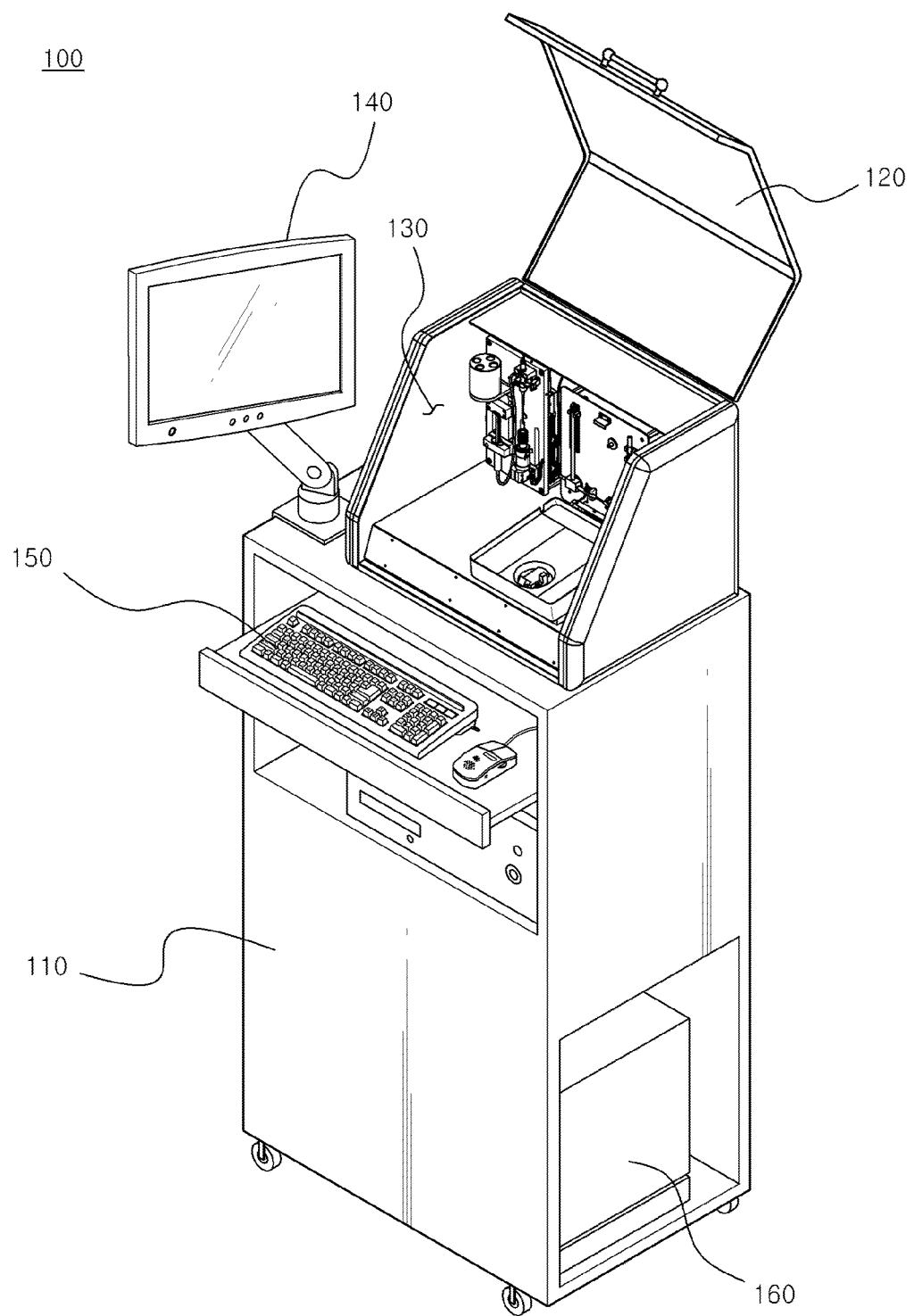
FIG. 3 is a frontal perspective view illustrating an example of a use of the viscosity measurement device of FIG. 2.

Referring to FIGS. 2 and 3, a device 100 for measuring a viscosity comprises a base body 110, a control part 160, and a display part 140. A stage 130 is formed on the base body 110. A transferring part 200 and viscosity measuring part 400 (see, e.g., FIG. 4) are provided on the stage 130. The stage 130 may be open or closed selectively by a cover 120. For example, the stage 130 may be closed by the cover 120 while operating the device, and temporarily opened in case of setting or changing needles or other parts. The control part 160 may be a conventional personal computer or other control device, and may have an input part 150 such as a keyboard, a mouse, and a wire/wireless data reading device, which are installed in (e.g., positioned within) the base body 110. The display part 140 may be a general monitor or other display device, and may have a printing function or module.

An operator may open the cover 120 to change a reservoir, a double needle delivery system, or a resistance tube (U-tube), and may initiate operation of the device 100 after closing the cover 120. Alternatively, the device 100 may initiate operation by itself when the cover 120 is closed. The cover 120 may be formed using transparent material to show the operation of the device 100 when the cover is closed.

Figure 4:
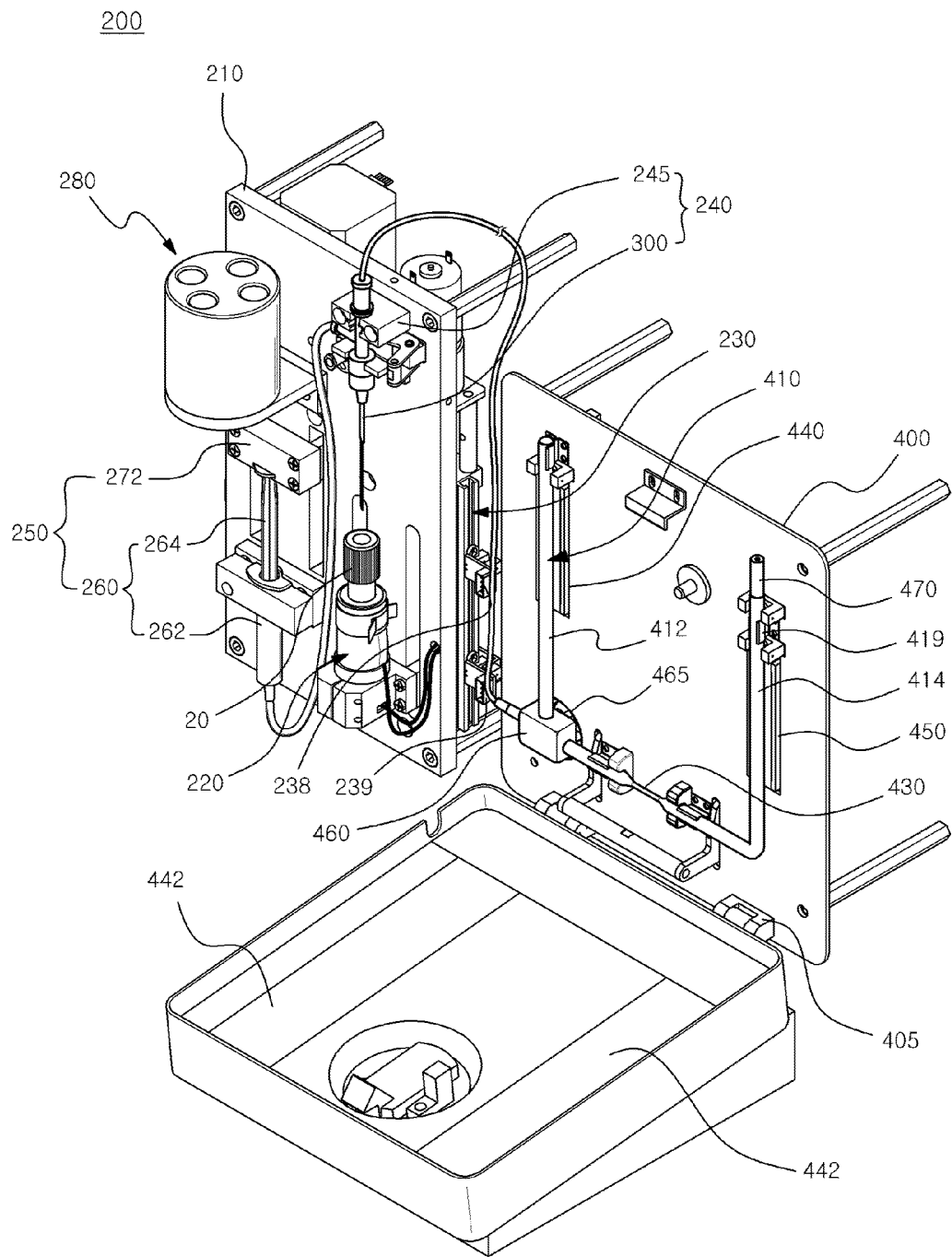
FIG. 4 is a frontal perspective view illustrating the transferring part and the viscosity measuring part of the viscosity measurement device of FIG. 2.
Figure 5:
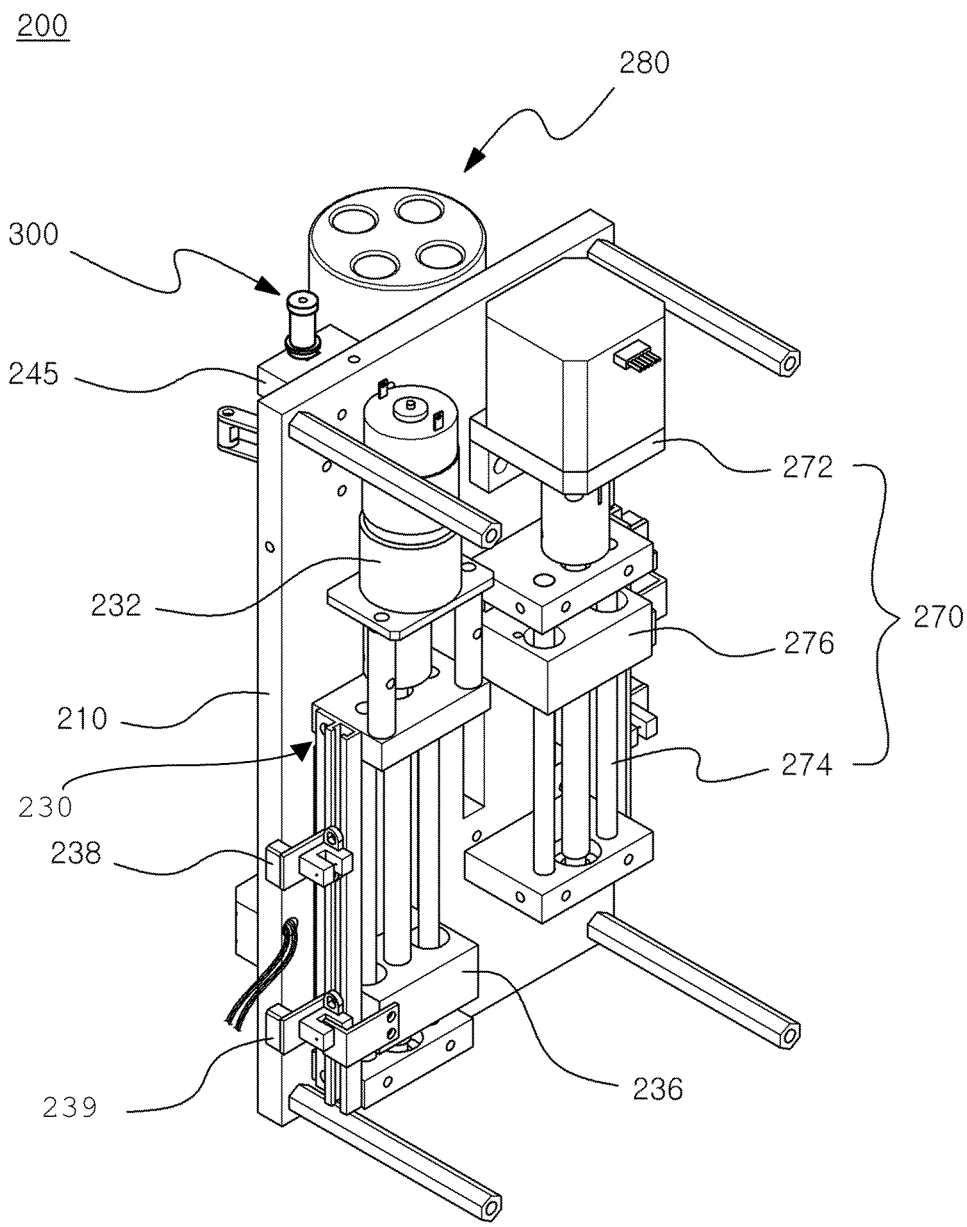
FIG. 5 is a rearward perspective view of the transferring part of FIG. 4.

Referring to FIGS. 4 and 5, the transferring part 200 automatically supplies blood from an evacuated reservoir 20 to the viscosity measuring part 400. The transferring part 200 includes a reservoir receiving member 220 for receiving the reservoir 20, a liquid supplying member 240 supplying the blood from the reservoir 20 to the viscosity measuring part 400, a distance adjusting member 230 adjusting the distance between a double needle section 300 and the reservoir 20, and a pressurized gas supply member 250 supplying air into the reservoir. These elements may be mounted on a base plate 210 to perform their functions simultaneously or in a predetermined order under the control of the control part 160. The viscosity measuring part 400 may measure the viscosity of the blood using flow resistance tubes or, alternatively, may measure the viscosity using other viscosity measuring methods.

The distance adjusting member 230 is mounted on the base plate 210 to move vertically, and the reservoir receiving member 220 is fixed on the distance adjusting member 230. As the distance adjusting member 230 moves vertically, the double needle section 300 may be inserted into or removed from the reservoir 20. Since the reservoir 20 has a silicone packing 25 on its top and the double needle section 300 has a sharp end, the double needle section 300 may be inserted into the reservoir 20 through the silicone packing. Alternatively, the reservoir 20 can move up toward the double needle section 300 so that the double needle section may be inserted into the reservoir 20 through the silicone packing 25.

In the present embodiment, the reservoir receiving member 220 is fixed to the distance adjusting member 230 while the distance adjusting member moves and the liquid supplying member 240 is fixed to the plate 210. Alternatively, in other embodiments, the sample liquid supplying member 240 can move relative to the plate 210 while the reservoir receiving member 220 is fixed to the plate. Of course, the sample liquid supplying member 240 and the reservoir receiving member 220 may be installed movably so that both members can approach toward each other.

The pressurized gas supply member 250 may supply a pressurized gas, such as air, and supply the gas at a constant pressure and/or flow. The illustrated pressurized gas supply member 250 supplies air using a syringe structure. In other embodiments, the pressurized gas supply member 250 supplies air using other pumping machines. According to the present embodiment, the pressurized gas supply member 250 comprises a syringe section 260 and a stepping driving motor section 270 (see, e.g., FIG. 5) moving a piston 264 of the syringe section 260. A cylinder 262 of the syringe section 260 is fixed on the base plate 210 and the piston 264 of the syringe section 260 moves vertically by a moving block 276 (see, e.g., FIG. 5) of the stepping driving motor section 270.

Referring to FIG. 5, the stepping driving motor section 270 further includes a stepping motor 272 and a block guide 274 for the moving block 276 along a slit in the base plate 210 in accordance with the rotation of the stepping motor 272. The stepping motor 272 may move the moving block 276 at a designated velocity to press the piston 264 using the moving block in a controlled velocity and length.

The distance adjusting member 230 may comprise a motor 232 and a mounting block 236 for holding the reservoir receiving member 220, and may move the mounting block 236 vertically using the driving force of the motor 232. Here, similar to the stepping driving section 270, the distance adjusting member 230 may use a rod guide or a ball screw to guide the linear movement of the block, and may use a stepping motor or a linear motor as the motor 232.

Figure 6:
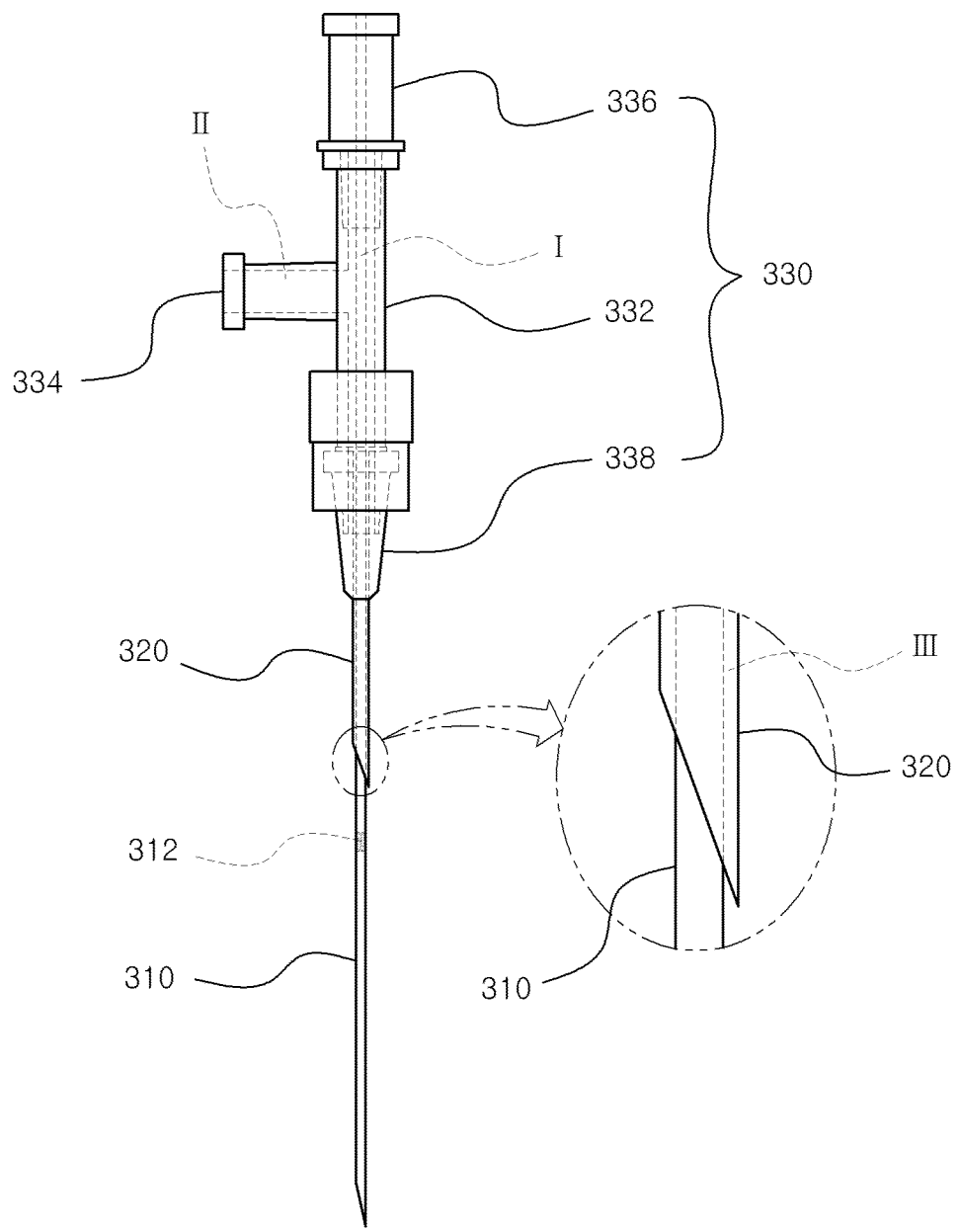
FIG. 6 is a side view illustrating a double needle section of a transferring part of a viscosity measurement device according to one embodiment of the present disclosure.

The liquid supplying member 240 includes the double needle section 300 and a needle fixing section 245 for fixing the double needle section 300 on the base plate 210. The needle fixing section 245 can temporarily fix the double needle section 300 for a viscosity measurement and release the double needle section 300 after the completion of each viscosity measurement so that a new double needle section may replace the previous double needle section. As shown in FIG. 6, the double needle section 300 has a double concentric cylindrical structure where an inner needle and an outer needle are arranged on the same axis, such that both needles of the double needle section 300 puncture through the silicone packing located at the top of the reservoir 20 to be inserted or removed simultaneously.

Note that the reservoir 20 in the present embodiment may be an evacuated tube (i.e., Vacutainer) for blood and may contain an anti-coagulant, such as EDTA, heparin or sodium citrate, for preventing blood from clotting or solidifying during sampling and while measuring blood viscosity. Moreover, in order to measure the viscosity of a relatively transparent liquid, for example blood plasma or serum, black dye or dark dye may be contained in the reservoir 20 to enhance the sensitivity of the liquid to an optical sensor. For example, if the evacuated reservoir contains edible black dye at a concentration of about 0.1~1% by volume to blood plasma or serum.

Figure 7:
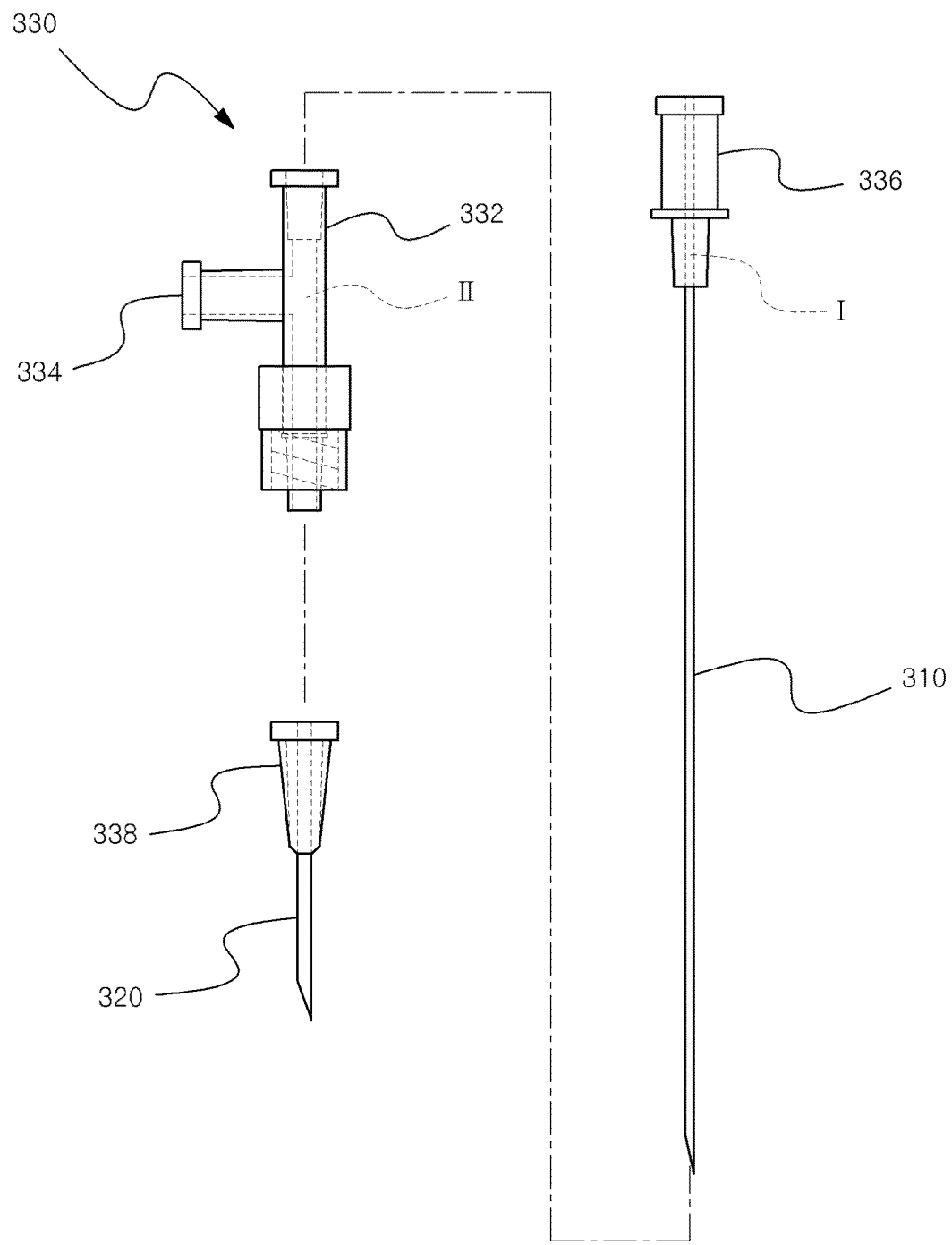
FIG. 7 is an exploded side view illustrating the double needle section of FIG. 6.

Referring to FIGS. 6 and 7, the double needle section 300 comprises an inner needle 310, an outer needle 320, and a fixing body 330. The inner needle 310 has a sharply cut end to penetrate a soft packing 25, and the outer needle 320 which is formed in a larger diameter than the inner needle 310 also has a sharply cut end receiving the inner needle 310.

The fixing body 330 may be formed by plastic injection molding. The inner needle 310 and the outer needle 320 may be fixed to the fixing body 330 via luer fittings, such as when manufactured by an insert injection molding technique. The fixing body 330 comprises a middle portion 332 forming a T-shaped path and an inner needle fixing portion 336 mounted at one end of the middle portion 332. The inner needle fixing portion 336 holds an end of the inner needle 310 to position the inner needle 310 through the middle portion 332. The fixing body 330 also includes an outer needle fixing portion 338 mounted at another end of the middle portion 332 against the inner needle fixing portion 336 and holding an end of the outer needle 320. As shown in FIG. 6, should the straightly connected path of the T-shaped path be arranged vertically, a top end of the straight path is engaged with the inner needle fixing portion 336 and a bottom end of the straight path is engaged with the outer needle fixing portion 338. The inner needle fixing portion 336 can be formed by injection molding with the inner needle 310. Moreover, a path I in the inner needle 310 can be separated from a path between the inner needle 310 and middle portion 332. The outer needle fixing portion 338 is fixed the bottom end of the middle portion 332 and the inner needle 310 passes through the center of the outer needle 320. Note that luer fittings may be used for all connections in the double needle section 300.

A path III for air may be formed between the outer needle 320 and the inner needle 310, and a path may be defined by an inlet 334 on a lateral side of the T-shaped middle portion 332 and an outlet portion on a bottom side of the middle portion 332. Air from the pressurized gas supply member is supplied via the inlet 334 of the double needle section 300 to supply pressurized gas to the reservoir 20 via the path II defined in the middle portion 330. The inner needle fixing portion 336 may be fixed to the top portion of the middle portion 332 by luer fitting or hook mechanism, and the outer needle fixing portion 338 may be fixed to the bottom portion of the middle portion 332 by luer fitting or thread coupling. In operation, moving the piston 264 in the pressurized gas supply member 250, air may be supplied into the reservoir 20 through paths II and III that are spatially connected to each other and the reservoir. As the air is supplied into the reservoir 20, the blood is pushed out of the reservoir 20 via the inner needle 310 and path I in the middle portion 330 to the viscosity measuring part 400.

The double needle section 300 may be mounted to the transferring part 200 for automatic operation. However, the double needles may be used in other viscosity devices which are operated automatically or manually. Because the double needle section 300 has a concentric structure, it is easy to insert and remove the needles from a reservoir simultaneously.

Figure 8:
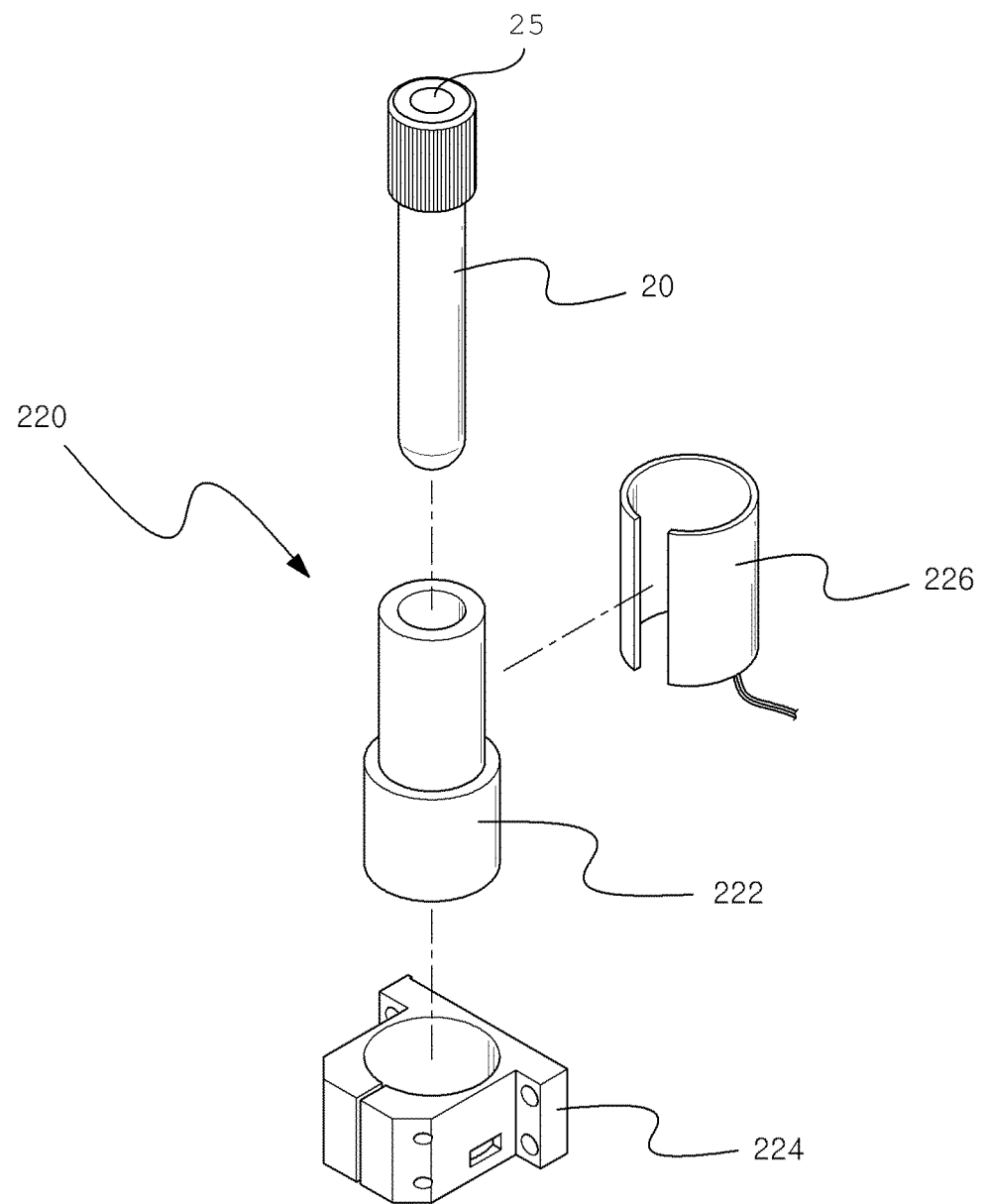
FIG. 8 is an exploded perspective view illustrating a reservoir receiving member of a viscosity measurement device according to one embodiment of the present disclosure.

Referring to FIG. 8, the reservoir receiving member 220 comprises a receiving portion 222 for receiving the reservoir 20, a holder 224 for fixing the receiving portion 222 to the distance adjusting member 230, and a thermostat or heater 226 maintaining a desired temperature (e.g., between about 36° C. and about 37° C.) around the receiving portion 222. The thermostat 226 may be provided as a silicone heater to be mounted around the reservoir 20 by a coupling means such as a binding clip. The control part 160 may maintain the temperatures of the receiving portion 222 and the reservoir 20 by controlling the thermostat 226, such that the viscosity of the blood is not affected by changing temperature while measuring the viscosity.

Figure 9:
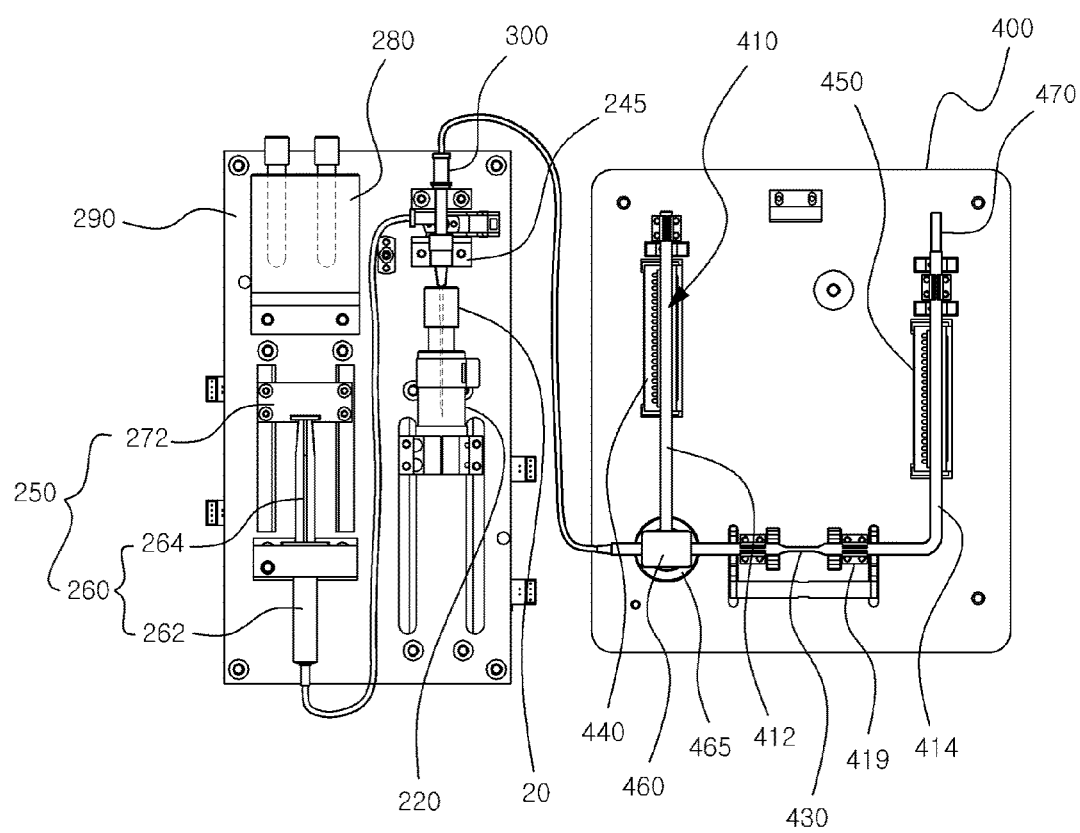
FIG. 9 is a front view illustrating the viscosity measuring part of FIG. 4.

Referring back to FIG. 4, the reservoir 20 may contain the evacuated liquid (e.g., blood) while remaining fixed to the reservoir receiving member 220. The reservoir receiving member 220 may move vertically with the reservoir 20 by the distance adjusting member 230. As shown in FIG. 9 in a vertically raised position, as the reservoir 20 moves up, the needles 310 and 320 in the double needle section 300 are inserted through the silicone packing 25 into the reservoir 20. In certain implementations, the distance adjusting member 230 may sense the location of the reservoir 20 using sensors 238 and 239, and move the reservoir 20 up until the inner needle 310 is partially submerged into the blood while the outer needle 320 is not submerged. To provide more efficient control and sensing of the position of the double needle section 300, the inner needle 310 or the outer needle 320 may have a mark on it. The reservoir receiving member 220 may move the reservoir 20 up and down by sensing the mark, and may use the position of the mark to adjust the position of the reservoir 20 to supply blood.

Since both the inner needle 310 and the outer needle 320 are arranged concentrically on the same axis, the two needles 310 and 320 can mechanically support each other, thus reducing the risk of being bent or folded when the reservoir 20 moves up. Thus, the processes of inserting or removing the two needles 310 and 320 are more simple and safe compared to previous devices.

As shown in FIG. 9, another thermostat or heater member 280 may be provided on the base plate 210. The thermostat member 280 is for temporarily holding additional reservoirs containing blood in queue for the purpose of preheating and expediting the testing of multiple samples by maintaining the temperature of the liquid samples within a desired temperature range (e.g., between about 36° C. and about 37° C.). The thermostat member 280 can maintain the liquid temperature within the desired temperature range so that the viscosity or other properties of standby bloods may not be affected by a change in temperature. Although the illustrated thermostat member 280 has four receiving holes for the storage of four liquid reservoirs, the number or shapes of the thermostat member or its number of holes may be modified in various ways. The location of the thermostat member 280 may be in any of various locations, for example on the base plate 210 or on the stage.

Figure 10:
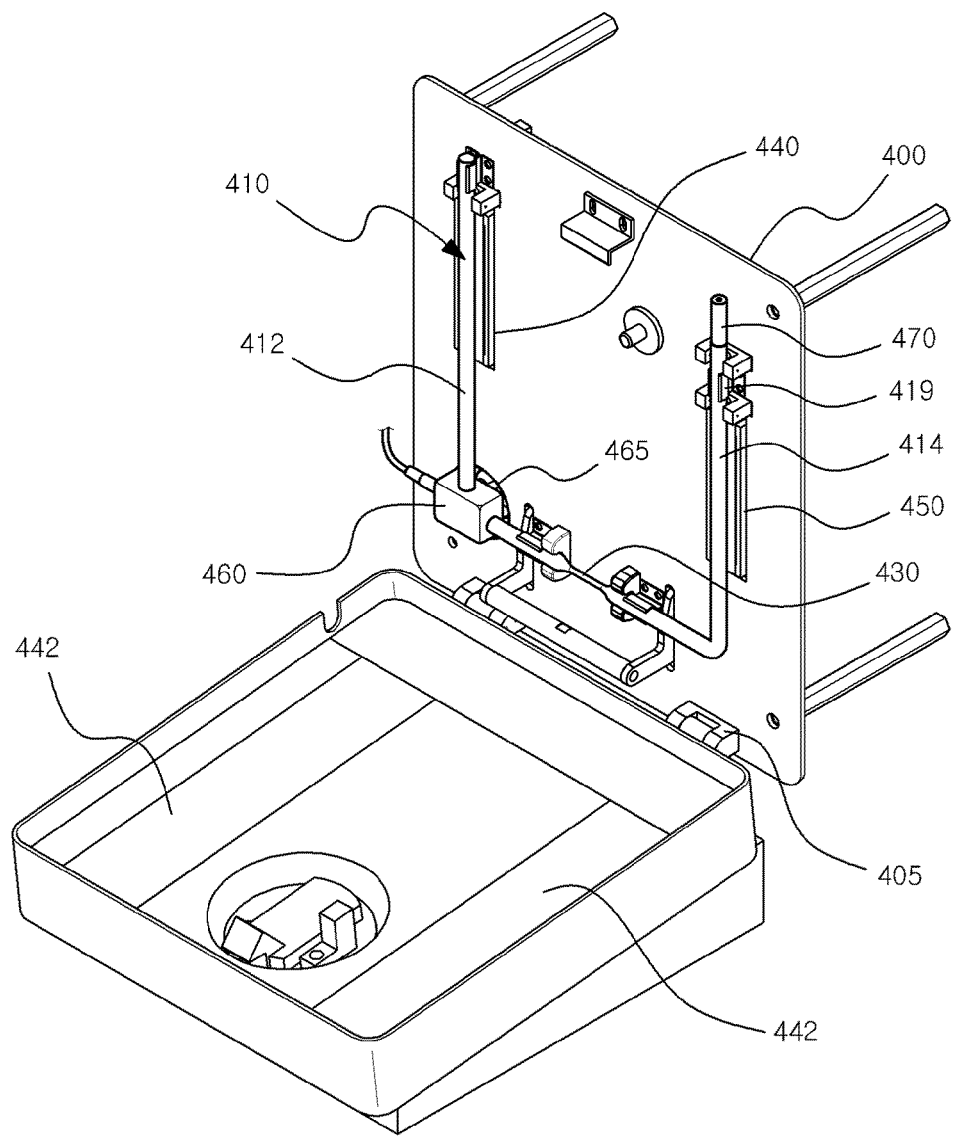
FIG. 10 is a perspective view of the viscosity measuring part of FIG. 9.

Referring to FIGS. 4, 9, and 10, the viscosity measuring part 400 may comprise two vertical resistance tubes 412 and 414, a 3-way stopcock valve 460 for selectively supplying blood to the vertical resistance tubes 412 and 414, a capillary section 430 provided on one of the vertical resistance tubes 412 and 414 or a connecting portion of the tubes, and optical sensors 440 and 450 positioned adjacent to the vertical resistance tubes 412 and 414, respectively, to detect the change with respect to time in a height of the blood in each tube.

The vertical resistance tubes 412 and 414 may be a U-tube 410, the lower end portions of which are spatially connected in U-shape. Alternatively, the resistance tubes 412 and 414 may be provided as an assembly where the 3-way valve 460 is mounted at the connecting portion of the tubes. The vertical resistance tubes 412 and 414 may be fixed on the base plate 210 by fixing brackets 419. The tubes 412 and 414 may be single-use disposable tubes, and may be replaced by a new set of resistance tubes after the completion of each viscosity measurement.

The vertical resistance tubes 412 and 414 may be connected by the 3-way valve 460. The valve 460, which is for controlling the supply of blood, can stop the flow of the blood and/or change the flow path. The 3-way valve 460 provided at the lower portion of the resistance tube 412, supplies the blood from the transferring part 200 to the resistance tube 412 until blood reaches a predetermined height at the resistance tube 412. Once the blood reaches the predetermined height at the tube 412, the 3-way valve 460 stops the blood flow to the tube 412 and supplies the blood to the other resistance tube 414 via capillary section 430 until blood reaches another predetermined height at the tube 414. Once the blood reaches the predetermined height at the tube 414, then the 3-way valve 460 disconnects the transferring part 200 from the viscosity measuring part 400. Subsequently, the 3-way valve connects the two resistance tubes 412 and 414 so that the blood begins to flow from the tube 412 to the tube 414 via the capillary section 430. The 3-way valve 460 may be controlled by a solenoid actuator 465 built in the viscosity measuring part 400. The solenoid actuator 465 and 3-way valve 460 can be controlled using the control part 160.

The optical sensors 440 and 450 may be provided as LCD-CCD arrays positioned along the vertical resistance tubes 412 and 414. The optical sensors 440 and 450, which are for detecting the movement (i.e., height variations) of the blood in the tubes 412 and 414, may be used to sense the change of liquid level of the blood with time.

According to the present disclosure, the viscosity measuring part 400 has a front cover, the bottom of which is engaged with a hinge 405 to selectively expose the tubes 412 and 414, and the optical sensors 440 and 450 positioned vertically behind the tubes. The front cover may include reference plates 442 or reflecting plates in accordance with the optical sensors 440 and 450, in order to enhance the detectability of the sensors when the front cover is closed. Alternatively, one can use different kinds of optical sensors, such as photoemitters and photodetectors arranged at the center of the resistance tube.

Figure 11:
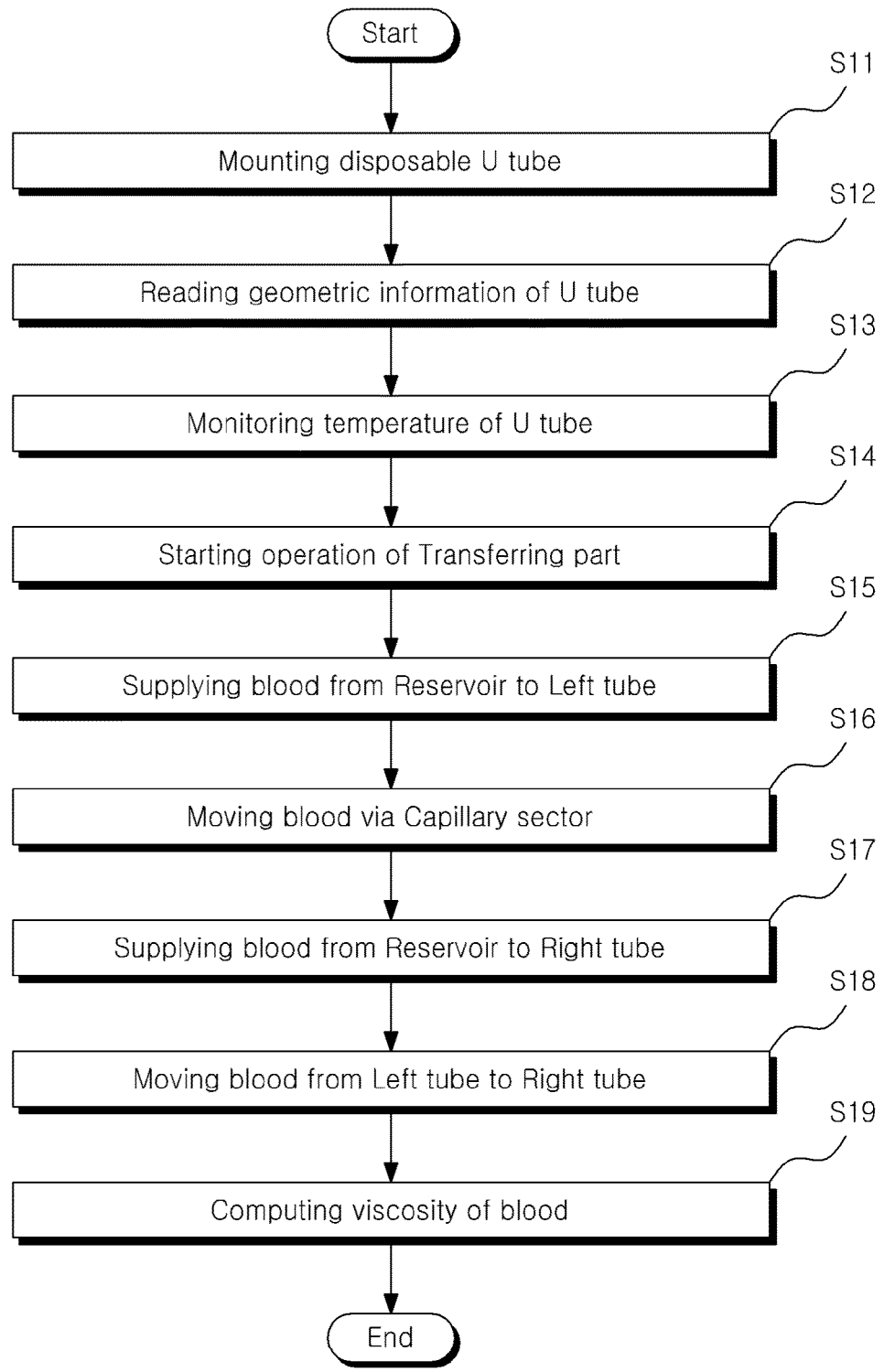
FIG. 11 is a flow chart illustrating the processes of measuring a viscosity of a fluid according to one embodiment of the present disclosure.

Hereinafter, a method for measuring the viscosity of blood using the viscosity measurement device 100 according to the present disclosure is described. FIG. 11 is a flow chart illustrating one method for measuring the viscosity using the device according to one embodiment. According to the method, a disposable U tube 410 may be mounted to the fixing bracket 419 of the viscosity measuring part 400, and the viscosity measuring part 400 may read the changing fluid level information from the U tube 410 (S11). In the present embodiment, a radio-frequency identification (RFID) tag 470 or a similar device such as one-wire system may be mounted on one end of the U tube 410 (i.e., at the end of tube 414), and a RFID reader (not shown) may read geometric information about the U tube 410, such as diameters and lengths of both the resistance tube and the capillary (S12).

A temperature sensor may be provided in the fixing bracket 419 or other point of the viscosity measuring part 400, to continuously monitor the temperature of the blood in the U tube (S13). The illustrated method is designed to start the transferring part 200 (S14) when the temperature sensor measures a predetermined designed temperature, for example, 36.5° C. The 3-way valve 460 connects the transferring part 200 to the left tube 412 at first, to supply the blood to the left tube 412 (see (a) in FIG. 12). Note that the transferring part 200 supplies the blood to the left tube 412 until the blood reaches a predetermined height 416 (see (b) in FIG. 12) in the tube 412. The height of the blood is measured by the optical sensor 440.

Figure 12:
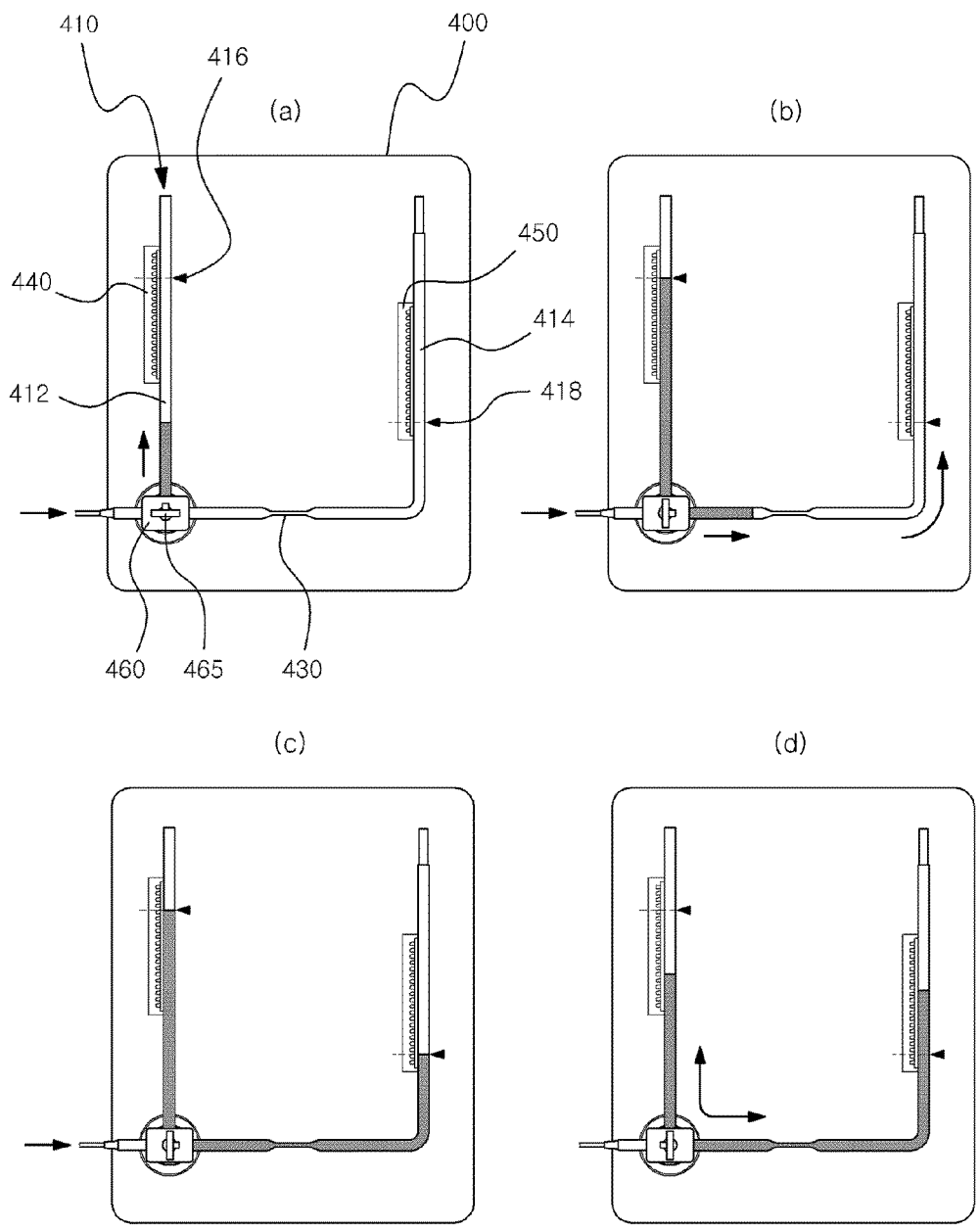
FIG. 12 gives front views illustrating the operating sequences of a viscosity measuring part of a viscosity measurement device according to one embodiment of the present disclosure.

After supplying the blood to the left tube 412, the 3-way valve 460 disconnects the tube 412 and connects the transferring part 200 to the right tube 414, to supply the blood to the right tube 414 via the capillary section (S16) (see (b) in FIG. 12). The blood is supplied to the right tube 414 until blood reaches another predetermined height 418 at tube 414, as the optical sensor 450 continues to monitor the height of the blood in the tube 414 (S17) (see (c) in FIG. 12).

Once blood reaches predetermined heights at both tubes 412 and 414, the 3-way valve 460 shuts the supply of the blood from the transferring part 200 by disconnecting the transferring part 200 from the viscosity measuring part 400 and connects the left and right tubes 412 and 414. As a result, the blood in the left tube 412 starts to move to the right tube 414 via the capillary section 430 (S18) (see (d) in FIG. 12). The method then computes the viscosity of the blood based on the change in height of the blood in at least one of the right and left tubes as a function of time (S19).

Figure 13:
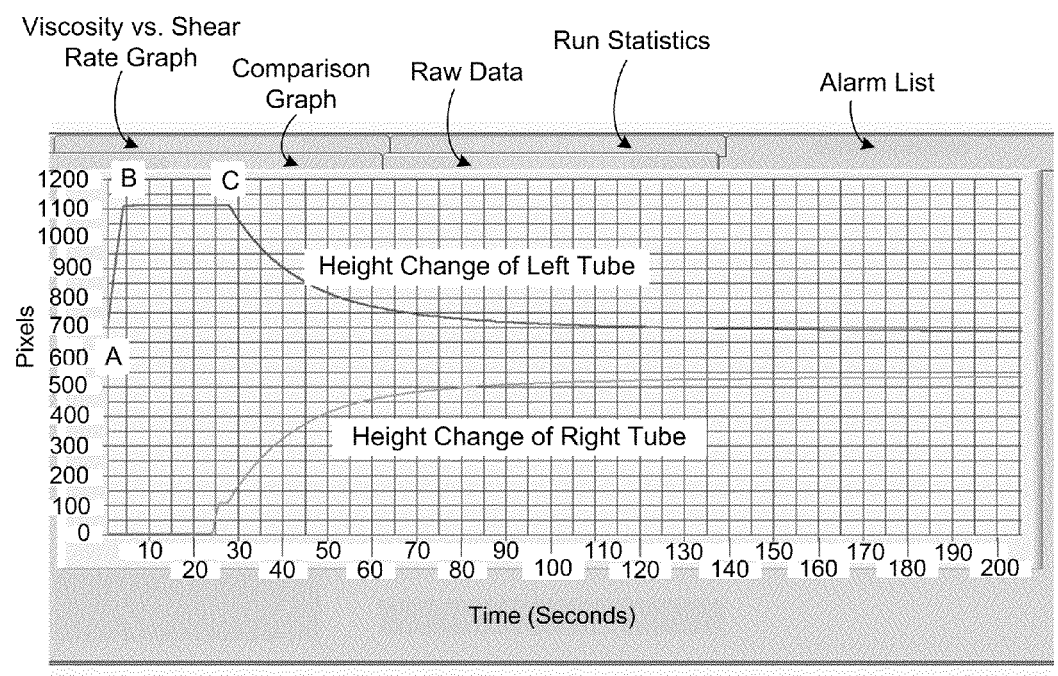
FIG. 13 is a graph showing results obtained from an optical sensor in the viscosity measuring part of one embodiment of a viscosity measurement device.

The changes in the height of blood as a function of time, at both tubes 412 and 414, are shown in FIG. 13. Referring to FIG. 13, the x axis represents time (seconds) and the y axis represents pixel numbers as measured by the optical sensors 440 and 450. It is important to note that, when supplying blood to the left tube 412, the optical sensor 440 (LCD-CCD array) detects the changes in the blood height with time and transmits the sensing result (h(t)) to the control part 160. If the blood is supplied at a high flow velocity, the optical sensor 440 may not be able to read the changes in the height accurately. This can happen in manual operation as in the prior art when an operator introduces the blood sample into the tube 412 at a high velocity beyond an optimum value as shown in FIG. 1. For example, unskilled operators usually do not know exactly how slowly or how quickly they should supply the blood to the tube 412. When the sample blood is introduced too fast, the optical sensor 440 cannot accurately read the changes in fluid height in the tube 412, resulting in a system error, and forcing the viscosity measuring part 400 to suspend the operation. On the contrary, if the blood is supplied too slowly, it also produces system error because the algorithm for calculating the viscosity should be completed in a predetermined time (i.e., about 3 minutes). Thus, in this case, there is not enough time for measuring height changes and transmitting the height change data to computer.

Note that in FIG. 13, the point A represents the time when the blood starts to be supplied from the transferring part 200 to the left tube 412, the point B represents the time when the blood reaches the predetermined height 416 at the tube 412. Here, it is preferable that the slope of the curve between the points A and B should not be too big or too small. Therefore, the air from pressurized-gas supply member 250 should be supplied into the reservoir 20 in an optimized velocity under the control of the control part 160 such that the blood should be introduced to the tube 412 at a proper velocity for a desired performance of the optical sensor 440 (i.e., to measure the viscosity of the blood successfully without a system error).

After the point B, the 3-way valve 460 connects the transferring part 200 to the capillary section 430 and the tube 414 such that the blood moves from the reservoir 20 to the right tube 414 via the capillary section 430. Accordingly, between the points B and C, the height of the blood in the left tube 412 does not change as indicated by a flat line (see top curve). During this time period, the height of the blood in the right tube 414 indicates zero since the blood has not reached the right tube 414 yet. The point C represents the time when the blood begins to fall at the left tube 412. When the blood eventually reaches the predetermined height 418 in the tube 414, the 3-way valve disconnects the transferring part 200 from the viscosity measuring part 400 and connects the left and right tubes 412 and 414 together, allowing the blood to move from the left tube 412 to the right tube 414 via the capillary section 430. From this point, the height of the blood in the left tube 412 gradually decreases as indicated in the graph after the point C, whereas the height of the blood in the right tube 414 gradually increases.

Although only a few embodiments of the present invention have been shown and described, the present invention is not limited to the described embodiments. Instead, as would be appreciated by those skilled in the art, changes may be made to these embodiments without departing from the principles of the invention, the scope of which is defined by the claims and their equivalents.

What is claimed is:

1. A device for automatically taking out a sample liquid contained in a reservoir and measuring the viscosity of the liquid, the device comprising:
  a base body;
  a transferring part provided on a stage of the base body, for taking the sample liquid out of the reservoir and supplying the sample liquid, the transferring part comprising (i) a reservoir receiving member for receiving the reservoir, (ii) a liquid supplying member including a needle section positioned adjacent to the reservoir received in the reservoir receiving member and a needle fixing section for fixing the needle section, for supplying the sample liquid from the reservoir to the viscosity measuring part, (iii) a distance adjusting member for adjusting the distance between the reservoir and the needle section; and (iv) a pressurized gas supply member for supplying a pressurized gas into the reservoir through the needle section;
  a viscosity measuring part provided on the stage, for measuring the viscosity of the sample liquid supplied from the transferring part;
  a control part for controlling operations of the transferring part and the viscosity measuring part; and
  a display part for displaying the result measured by the viscosity measuring part.

2. The device of claim 1, wherein the reservoir receiving member comprises a receiving portion receiving the reservoir and a thermostat part maintaining the receiving portion at a predetermined temperature.

3. The device of claim 1, wherein the reservoir receiving member is mounted on the distance adjusting member, moves forward or backward to the needle section to have the needle section be inserted into or removed from the reservoir.

4. The device of claim 1, wherein the needle section comprises,
  an inner needle which is elongated and hollow;
  an outer needle receiving the inner needle to form a fluidic path for the pressurized gas; and
  a fixing body to fix the inner needle and the outer needle, which provides a path connecting the inner needle and the viscosity measuring part and another path connecting the fluidic path for the pressurized gas via the outer needle and the pressurized gas supply member.

5. The device of claim 4, wherein the fixing body comprises a middle portion forming a T-shaped path, an inner needle fixing portion mounted at one end of the middle portion and holding an end of the inner needle to position the inner needle through the middle portion, and an outer needle fixing portion mounted at another end of the middle portion against the inner needle fixing portion and holding an end of the outer needle,
  wherein the outer needle receives the inner needle when the outer needle fixing portion is mounted at the other end of the middle portion, and
  wherein, via the other end of the middle portion, the pressurized gas is supplied through the fluidic path formed between the outer needle and the inner needle.

6. The device of claim 5, wherein the outer needle fixing portion is mounted at the other end of the middle portion by at least one of a luer fitting or threaded coupling.

7. The device of claim 1, wherein the pressurized gas supply member comprises a syringe section and a stepping driving section moving a piston at the syringe section, and the pressurized gas in the syringe section is supplied to reservoir in the reservoir receiving member via a nozzle of the syringe section and the needle section.

8. The device of claim 1, wherein the transferring part further comprises a thermostat member which is capable of keeping the reservoir at a predetermined constant temperature.

9. The device of claim 1, wherein further comprising a cover for opening and closing the stage.

10. The device of claim 1, wherein the reservoir is an evacuated tube.

11. The device of claim 1, wherein the reservoir contains anti-coagulation material for preventing the coagulation of the sample liquid while measuring the viscosity of the sample liquid.

12. The device of claim 11, wherein the anti-coagulation material comprises at least one of EDTA, heparin, or sodium citrate.

13. The device of claim 1, wherein the reservoir contains dye to enhance the sensitivity of the sample liquid to an optical sensor while measuring the viscosity of the sample liquid.

14. The device of claim 1, wherein the viscosity measuring part comprises two vertical resistance tubes, of which their lower end portions are connected to each other, a valve for supplying the sample liquid to the vertical resistance tubes, a capillary section provided on one of the vertical resistance tubes or a connecting portion of the tubes, and two optical sensors positioned adjacent to the two vertical resistance tubes, respectively, to detect the change in the height of the sample liquid in each tube with time.

15. The device of claim 14, wherein the valve is a 3-way valve, which supplies the sample liquid by the transferring part to the two vertical resistance tubes one at a time, forms a predetermined difference in the fluid levels of the sample liquid, stops the supply of the sample liquid to the vertical resistance tubes, and spatially connects the two vertical resistance tubes to make the sample liquid move from one resistance tube to another tube using the difference in fluid levels.

\* \* \* \* \*